United States Patent [19]

Goto

[11] 4,404,852
[45] Sep. 20, 1983

[54] FROST SENSOR

[75] Inventor: Norio Goto, Tokyo, Japan

[73] Assignees: Hitachi, Ltd.; Hitachi Metals, Ltd.; Research Development Cooperation of Japan, all of Tokyo, Japan

[21] Appl. No.: 276,816

[22] Filed: Jun. 24, 1981

[30] Foreign Application Priority Data

Jun. 25, 1980 [JP] Japan .................................. 55-85095

[51] Int. Cl.³ ............................................. G01N 29/00
[52] U.S. Cl. ...................................... 73/599; 340/582
[58] Field of Search ......................... 73/599, 590, 643; 340/582; 310/313 R, 313 B

[56] References Cited

U.S. PATENT DOCUMENTS 2,414,756  1/1947  May ..................................... 340/582
2,789,281  4/1957  Short et al. ......................... 340/582
4,335,613  6/1982  Luukkala .............................. 73/599

Primary Examiner—Anthony V. Ciarlante
Attorney, Agent, or Firm—Antonelli, Terry & Wands

[57] ABSTRACT

A frost sensor for detecting the presence of frost uses an acoustic device having an acoustic transmitting medium made of a magnetostrictive material, particularly an amorphous metal alloy, of a ribbon shape, as means for detecting the frost.

11 Claims, 10 Drawing Figures

FROST SENSOR

BACKGROUND OF THE INVENTION

1. Field of the Invention

The present invention relates to a frost sensor (frost detector), and more particularly to a frost sensor suitable for detecting frost deposited on a refrigerator (evaporator) of a refrigerating machine, a freezer, a room air conditioner or the like.

2. Description of the Prior Art

Optical and mechanical means have been known as means for detecting frost deposited on an article. The optical means detects the presence of frost deposited on the article by a difference of a light transmission or light reflection between a frosted state and a non-frosted state. Since the optical means can be constructed by a photo-transistor and a light emitting diode, the structure is simple. However, since the light transmission or light reflection changes when a surface of the article is contaminated or depending on the shape of frost deposited on the article surface, it is difficult to exactly detect the presence of frost. The mechanical means uses a contact probe (piece), for example, to detect the thickness of frost deposited on the article to detect the presence of frost. The mechanical means can directly detect the presence of frost but it must include means for moving the contact probe (piece) to adjust the position thereof. It is, therefore, complex in structure. It usually includes a movable member to detect the contact of the contact probe (piece) to the frost. Since the movable member is apt to be frozen by the frost, exact detection of frost is difficult. In addition, the adjustment of position of the contact probe (piece) is not easy.

Means for detecting frost deposited on a refrigerator of a room air conditioner is disclosed in the U.S. Pat. No. 3,466,888. In the disclosed detection means, the temperature of the refrigerator and the ambient temperature are sensed by a pair of thermistors to detect a change in the difference between those temperatures. It indirectly detects the presence of frost but does not detect the frost directly. Accordingly, it is difficult to precisely (with high sensitivity) detect the presence of frost.

Thus, the prior art frost sensors exhibit many disadvantages.

SUMMARY OF THE INVENTION

It is an object of the present invention to provide a frost sensor which is simple in structure and can detect the presence of frost directly and electrically with a high sensitivity.

The frost sensor in accordance with the present invention utilizes an acoustic device having an acoustic transmitting medium made of magnetostrictive material of ribbon shape. In general, in the present acoustic device, transducers are disposed at opposite ends of the acoustic transmitting medium of the magnetostrictive material, and an electrical signal is supplied to one of the transducers to generate an acoustic wave (sound wave) in the acoustic transmitting medium. The acoustic wave is retransduced to an electrical signal by the other transducer. Such an acoustic device has been known by U.S. Pat. No. 3,838,365. In this type of acoustic device, when the frequency of the electrical signal supplied to the transducer is properly selected, a LAMB wave which is a special acoustic wave as will be explained later is generated. It has been found that when a solid is deposited on the surface of the acoustic transmitting medium, the LAMB wave is reflected by the solid and does not reach the other transducer. Thus, when the frost is deposited on the surface of the acoustic transmitting medium, the LAMB wave is reflected by the frost. Accordingly, by measuring the magnitude of the signal arriving at the other transducer, the presence of frost can be detected. This is a basic principle of the present invention.

An amorphous metal alloy is most suitable for the acoustic transmitting medium. The amorphous metal alloy is a superior ultrasonic wave transmitting medium because it can be readily formed into a ribbon shape having a thickness of 10–50 $\mu$m, can readily transmit the acoustic wave and exhibits a small transmission loss for the acoustic wave (approximately 0.05 dB/cm at 500 KHz). The amorphous metal alloy has a large magnetostriction constant of approximately $30 \times 10^{-6}$, has a large permeability while it is a magnetostrictive material and has a large electrical signal-to-mechanical signal or acoustic wave transducing coefficient of approximately 0.68. It can, therefore, form a superior transducer. The volume resistivity p of the amorphous metal alloy is approximately 120 $\mu\Omega$-cm which is roughly one order larger than that of nickel. Accordingly, an eddy current hardly flows therethrough and hence a power loss is low even when an electrical signal of a high frequency is supplied to the transducer. Since the acoustic transmitting medium is of ribbon or belt shape, it is hereinafter referred to as a magnetostrictive ribbon.

When a wavelength of the electrical signal supplied to the transducer is suffficiently shorter than the thickness of the magnetostrictive ribbon, an acoustic wave transmitted through the magnetostrictive ribbon is the LAMB wave which is intermediate a surface wave and a bulk wave. The surface wave is highly affected by an article deposited on the surface of the magnetostrictive ribbon. For example, when liquid such as water droplet deposits on the surface of the magnetostrictive ribbon, the surface wave cannot fully propagate. The bulk wave is substantially unaffected by an article deposited on the surface of the magnetostrictive ribbon. Accordingly, even when frost deposits on the surface of the magnetostrictive ribbon, it fully propagates through the magnetostrictive ribbon. The LAMB wave has an intermediate property of the surface wave and the bulk wave and hence it is adequately affected by the article deposited on the surface of the magnetostrictive ribbon. When liquid such as a water droplet deposits on the surface of the magnetostrictive ribbon, the LAMB wave is not reflected by the water droplet but propagates through the magnetostrictive ribbon. However, when a solid such as frost deposits on the surface of the magnetostrictive ribbon, the LAMB wave is reflected by the frost and does not propagate through the magnetostrictive ribbon. In the frost sensor of the present invention, the LAMB wave propagates through the magnetostrictive ribbon.

DESCRIPTION OF THE PREFERRED EMBODIMENTS

Figure 1:
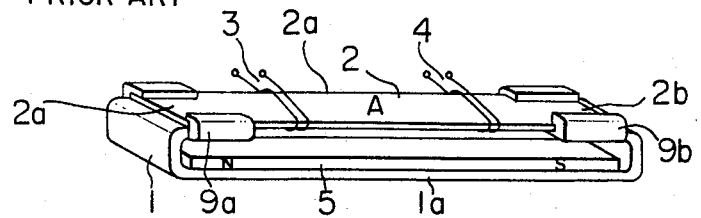
FIG. 1 shows a perspective view illustrating a principal structure of a frost sensor.

FIG. 1 shows a principal structure of a frost sensor in accordance with the present invention. In the present frost sensor, a magnetostrictive ribbon 2 has its opposite ends 2a and 2b fixed to a support member 1 having a C-shaped cross-section by supports 9a and 9b of the support member 1. A first coil 3 and a second coil 4 are mounted on the magnetostrictive ribbon 2. The first coil 3 is an acoustic wave exciting coil for generating an acoustic wave (LAMB wave) in the magnetostrictive ribbon 2 and it forms a transducer which generates the acoustic wave in the magnetostrictive ribbon 2 in response to an electrical signal flowing through the first coil 3. The second coil 4 is a detection coil for detecting the acoustic wave propagating through the magnetostrictive ribbon 2 and it forms a transducer which retransduces the acoustic wave to an electrical signal. It should be understood that the first coil 3 may be the detection coil and the second coil 4 may be the exciting coil.

A permanent magnet 5 is fixedly mounted on a bottom 1a of the support member 1. The permanent magnet 5 generates a biasing magnetic field in the magnetostrictive ribbon 2 by magnetic fluxes which the permanent magnet 5 generates. The permanent magnet 5 may have an N-pole and an S-pole arranged lengthwise as shown in FIG. 1 or may have those poles arranged widthwise. It is preferable that both poles are arranged to generate the biasing magnetic field such that a magnetic spin of the magnetostrictive ribbon 2 is oblique to an easy axis of magnetization of the magnetostrictive ribbon 2 by an angle of 45 degrees. The support member 1 is usually supported by a non-magnetic material so that a portion of the magnetic fluxes leaking from the N-pole of the permanent magnet 5 passes through the magnetostrictive ribbon 2 and reaches the S-pole of the permanent magnet 5. This flux portion forms the biasing magnetic field for the magnetostrictive ribbon 2.

Figure 2:
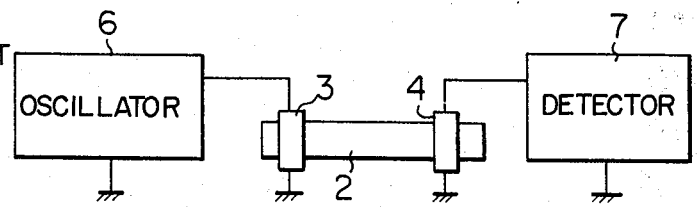
FIG. 2 shows a block diagram of a frost detector.
Figure 3:
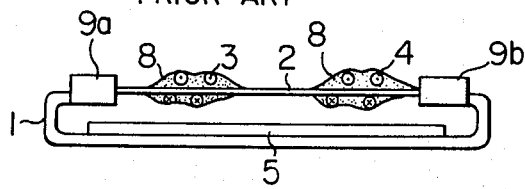
FIG. 3 shows a sectional view of a major portion illustrating the deposition of a water droplet on a coil in the frost sensor shown in FIG. 1.

Referring to FIG. 2, an oscillator 6 is connected to the coil 3 mounted on the magnetostrictive ribbon 2. When an R.F. current is supplied from the oscillator 6 to the coil 3, the magnetic fluxes pass through the magnetostrictive ribbon 2 by the current flowing through the coil 3. As a result, the magnetic spin vibrates to generate magnetostriction in the magnetostrictive ribbon 2. The magnetostriction causes an acoustic wave which imparts vibration to the magnetic spin and propagates through the magnetostrictive ribbon 2. When the acoustic wave arrives at the coil 4, the biasing magnetic field generated by the permanent magnet 5 varies by the vibration of the magnetic spin to generate a voltage in the coil 4. The voltage generated in the coil 4 is supplied to a detector 7 so that the R.F. electrical signal supplied from the oscillator 6 to the coil 3 is detected by the detector 7. If frost deposits at an area A on the magnetostrictive ribbon 2, the acoustic wave does not propagate through the magnetostrictive ribbon 2 and the acoustic wave does not substantially reach the coil 4. As a result, the voltage generated in the coil 4 is low and the electrical signal supplied from the oscillator 6 to the coil 3 is not detected by the detector 7. A portion of the magnetic fluxes generated by the current flowing through the coil 3 directly passes through the coil 4 to generate a voltage in the coil 4 whether or not the frost exists. Since this voltage is a noise voltage, it must be minimized as much as possible.

In the front sensor described above, the water droplet 8 readily deposits around the coils 3 and 4. The water droplet 8 is frozen to prevent the acoustic wave generated by the current flowing through the coil 3 from propagating so that the correct detection of the presence of frost is rendered difficult, because the ice resulting from the frozen droplet 8 is a solid like the frost and hence it reflects the acoustic wave.

If the coils 3 and 4 are wound on the magnetostrictive ribbon 2 at positions distant from the magnetostrictive ribbon 2, the propagation of the acoustic wave will not be prevented even if the water droplets deposited on the coils 3 and 4 are frozen. However, when the coils 3 and 4 are wound on the magnetostrictive ribbon 2 at positions distant from the magnetostrictive ribbon 2, the magnetic fluxes generated by the coil 3 and passing through the coil 4 increases so that the signal-to-noise (S/N) ratio of the electrical signal generated in the coil is lowered. The electrical signal Sig1 retransduced by the coil 4 from the acoustic wave transduced by the coil 3 is represented by;

$$Sig1 \approx (kS_3) \times (kS_3)$$

where $S_3$ is a cross-sectional area of the magnetostrictive ribbon 2 and k is a coupling coefficient of the acoustic wave and the electrical signal in the coils 3 and 4, and the signal Sig2 generated in the coil 4 by the magnetic fluxes generated in the coil 3 is expressed by;

$$Sig2 \approx (S_1 - S_3) \times (S_2 - S_3)$$

where $S_1$ is a cross-sectional area of the coil 3 and $S_2$ is a cross-sectional area of the coil 4. Accordingly, the S/N ratio is given by;

$$S/N = Sig1/Sig2$$
$$= k^2 S_3^2 / \{(S_1 - S_3) \cdot (S_2 - S_3)\}$$

Thus, as the sectional areas $S_1$ and $S_2$ of the coils 3 and 4 increase, the S/N ratio decreases. As the S/N ratio decreases, the exact detection of the presence of frost is harder.

The illustrated frost sensor directly detects the presence of the frost deposited on the area A of the magnetostrictive ribbon 2. The illustrated frost sensor detects the frost with a high sensitivity as will be explained later. Since it includes no mechanical adjusting part nor apparently mechanically moving part, it is simple in structure. In addition, the present frost sensor can electrically detect the frost.

In the frost sensor shown in FIG. 1, however, since the magnetic fluxes generated by the permanent magnet 5 pass through the entire length of the magnetostructure ribbon 2 resulting in a large magnetic flux density in the magnetostrictive ribbon 2, the magnetic fluxes generated by the current flowing through the coil 3 hardly pass through the magnetostrictive ribbon 2. As a result, the magnetostriction generated in the magnetostrictive ribbon 2 by the current flowing through the coil 3 is small. Consequently, a large current must be supplied to the coil 3 in order to generate a required magnetostriction.

While the frost sensor shown in FIG. 1 is simple in construction, it is hard to manufacture because the magnetostrictive ribbon 2 extends through the coils 3 and 4 and is fixed by the supports 9a and 9b of the support member 1. Since the magnetostrictive ribbon 2 is of belt shape having a very thin thickness, it is difficult to insert the magnetostrictive ribbon 2 through the coils 3 and 4, and the fixing of the magnetostrictive ribbon 2 having the coils 3 and 4 mounted thereon to the supports 9a and 9b must be carefully carried out such that the coils 3 and 4 are not broken.

Figure 4:
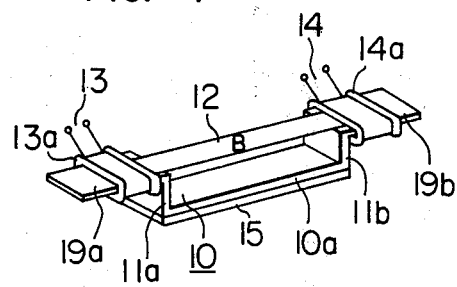
FIG. 4 shows a perspective view of a first embodiment of a frost sensor in accordance with the present invention.
Figure 5:
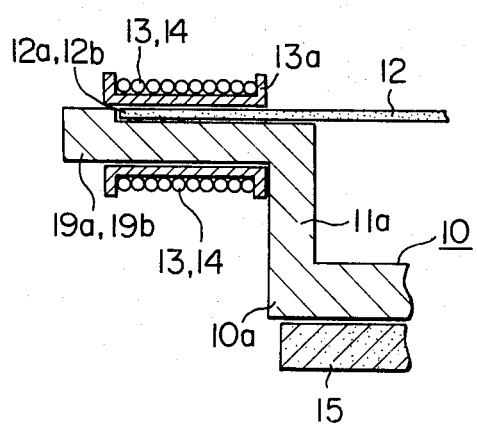
FIG. 5 shows a sectional view of a major portion of the frost sensor of FIG. 4.

A preferred embodiment of the frost sensor in accordance with the present invention is now explained. Referring to FIG. 4, the frost sensor of the present invention has a support member 10 which comprises a plate-shaped base 10a, a pair of legs 11a and 11b which extend from the opposite ends of the base 10a in the same direction and at a right angle to the upper plane of the base 10a, and supports 19a and 19b which project from ends of the legs 11a and 11b parallel to the base 10a and outwardly of the ends of the base 10a. As shown in FIG. 5, a magnetostrictive ribbon 12 is fixed to the supports 19a and 19b of the support member 10, and coils 13 and 14 wound on bobbins 13a and 14a are mounted on the supports 19a and 19b to wrap around the magnetostrictive ribbon 12 and the supports 19a and 19b. A permanent magnet 15 for generating a biasing magnetic field for the magnetostrictive ribbon 12 is fixed to the base 10a of the support member 10. The permanent magnet 15 may be fixed to a lower surface of the base 10a as shown in FIG. 4 or it may be fixed to the upper surface of the base 10a as shown in FIG. 1. The permanent magnet 15 may be magnetized lengthwise or it may be magnetized widthwise. In any case, it is preferable that the magnetic spin of the magnetostrictive ribbon 12 is oblique to the easy angle of magnetization of the magnetostrictive ribbon 12 by an angle of 45 degrees at the magnetostriction generating portion. The magnetostrictive ribbon 12 of the present frost sensor is made of an amorphous metal alloy consisting of iron, nickel, silicon and boron (Fe-Ni-Si-B) and has thickness of approximately 13 μm, width of 5 mm and length of 30 mm. The opposite end portions 12a and 12b each having a length of approximately 5 mm are fixed to the supports 19a and 19b. Each of the coils 13 and 14 is formed by urethane coated copper wire having a diameter of 0.12 mm and has approximately 50 turns. The support member 10 is made of brass having thickness of approximately 1 mm or it may be made of plastic material. The permanent magnet 15 is made of a mixture of rubber and ferrite powder and supplies a biasing magnetic field of 15 oersteads (Oe) (1200 AT/m) to the magnetostrictive ribbon 12. The present frost sensor detects frost deposited on an area B of the magnetostrictive ribbon 12.

In the present frost sensor shown in FIGS. 4 and 5, the magnetic fluxes generated by the permanent magnet 15 create the biasing magnetic field in the magnetostrictive ribbon 12 as described above. The magnetic fluxes emanate from one magnetic pole of the permanent magnets 15, pass through the magnetostrictive ribbon 12 and reach the other magnetic pole of the permanent magnet 15. As shown in FIG. 5, since the opposite ends 12a and 12b of the magnetostrictive ribbon 12 are disposed distantly from the permanent magnet 15, only a small amount of magnetic fluxes pass through the opposite ends 12a and 12b of the magnetostrictive ribbon 12 so that only weak biasing magnetic fields are created at the opposite ends 12a and 12b. As a result, a magnetic flux density in the magnetostrictive ribbon 12 caused by the permanent magnet 15 is small. Accordingly, when a current flows through the coil 13, the magnetic fluxes generated by the current pass through the magnetostrictive ribbon 12. Since the amorphous metal alloy has a high permeability, the magnetic fluxes readily pass through the end 12a of the magnetostrictive ribbon 12 and hence the magnetostriction is readily generated in the magnetostrictive ribbon 12. Thus, unlike the frost sensor shown in FIG. 1, the frost sensor shown in FIG. 4 readily generates the magnetostriction by the current flowing through the coil 13.

In the structure of the present frost sensor, only weak biasing magnetic fields are created at the opposite ends 12a and 12b. The permanent magnet 15 may be disposed close to the magnetostrictive ribbon 12 such that a strong magnetic field is applied only to a center portion of the magnetostrictive ribbon 12 excluding the opposite ends on which the coils 13 and 14 are mounted. When the strong magnetic biasing field is applied to the center portion of the magnetostrictive ribbon 12, the magnetic flux density in the magnetostrictive ribbon 12 increases so that the magnetic fluxes generated by the coil 13 do not reach the coil 14 through the magnetostrictive ribbon 12. As a result, the noise is reduced.

In the present frost sensor, the coils 13 and 14 are not disposed at the area B (center portion) of the magnetostrictive ribbon 12 through which the acoustic wave propagates. Accordingly, no water droplet is frozen at that area. Even if water droplets deposit on the coils 13 and 14 and are frozen, the acoustic wave is not reflected by the frozen water droplets because the ends 12a and 12b of the magnetostrictive ribbon 12 on which the coils 13 and 14 are mounted do not serve as the propagation area of the acoustic wave.

In the present frost sensor, since the coils 13 and 14 are fixed to the supports 19a and 19b after the magnetostrictive ribbon 12 has been fixed to the support member 10, it is easy to manufacture. In manufacturing the present frost sensor, the magnetostrictive ribbon 12 is first fixed to the support member 10 and then the coils 13 and 14 wound on the bobbins 13a and 14a are mounted on the supports 19a and 19b. The bobbins 13a and 14a have holes through which the supports 19a and 19b are inserted. The permanent magnet 15 may be fixed to the support member 10 before the magnetostrictive ribbon 12 is fixed to the support member 10 or after it has been fixed, or the permanent magnet 15 may be fixed after the coils 13 and 14 have been fixed to the support member 10.

The present frost sensor directly detects the frost, is simple in structure, has no part which requires adjustment and can electrically detect the frost.

The permanent magnet 15 may be a ferrite magnet or even an electromagnet. The magnetostrictive ribbon 12 may be made of a metal alloy consisting of iron, nickel, silicon, boron, chromium and phosphorus. Since this metal alloy is difficult to erode, it is suitable for use as the magnetostrictive ribbon 12 of the frost sensor.

Figure 6A:
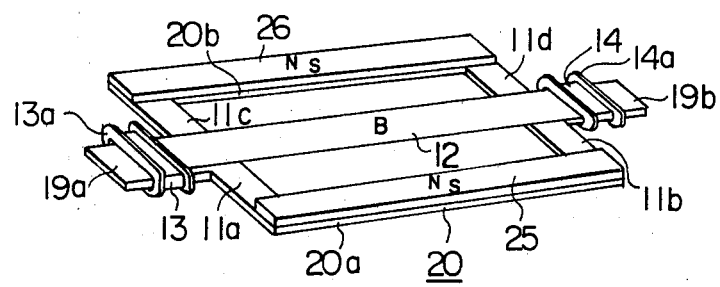
FIGS. 6a and 6b show perspective views of a second embodiment of the present invention.
Figure 6B:
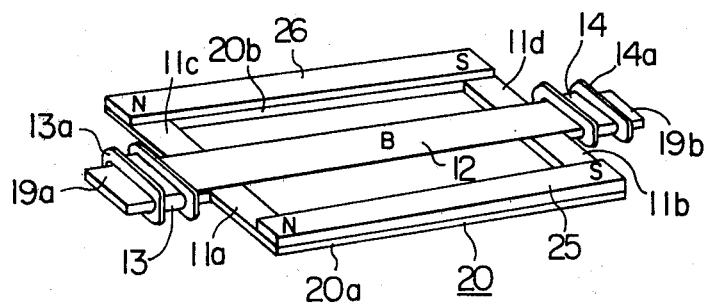

FIGS. 6a and 6b show a second embodiment of the frost sensor of the present invention. As shown in FIGS. 6a and 6b, the present frost sensor has a support member 20 of plate shape having laterally opposing bases 20a and 20b, legs 11a and 11c; and 11b and 11d extending from the respective opposite ends of the bases 20a and 20b at right angle to the sides of the bases 20a and 20b, the other ends of the respective leg pairs 11a and 11c; and 11b and 11d being coupled to each other, and supports 19a and 19b extending from the coupling areas of the legs 11a and 11c; and 11b and 11d in parallel to the bases 20a and 20b and outwardly of the bases 20a and 20b. Like in the frost sensor shown in FIG. 5, the magnetostrictive ribbon 12 is fixed to the supports 19a and 19b of the support member 20, and the coils 13 and 14 wound on the bobbins 13a and 14a are mounted on the supports 19a and 19b to wrap around the magnetostrictive ribbon 12 and the supports 19a and 19b. Permanent magnets 25 and 26 for generating a biasing magnetic field for the magnetostrictive ribbon 12 are fixed to the bases 20a and 20b of the support 20. The permanent magnets 25 and 26 may be fixed to the upper surface or the lower surface of the bases 20a and 20b. The permanent magnets 25 and 26 may be magnetized lengthwise or they may be magnetized widthwise. When they are magnetized widthwise, the permanent magnets 25 and 26 are arranged such that the N-poles and the S-poles face to each other as shown in FIG. 6a, and when the permanent magnets 25 and 26 are magnetized lengthwise they are arranged such that the N-poles face to each other and the S-poles face to each other as shown in FIG. 6b. The other arrangements are substantially identical to those shown in FIG. 4 and hence they are not explained here.

Figure 7:
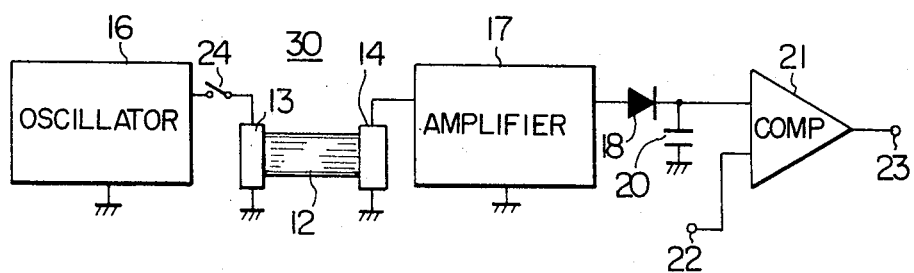
FIG. 7 shows a block diagram of a frost detector.

A frost detector which uses the present frost sensor is now explained. FIG. 7 shows a block diagram of the frost detector which uses the present frost sensor. The frost detector comprises a frost sensor 30, an oscillator 16 connected to the coil 13 of the frost sensor 30 to supply an A.C. signal to the coil 13 through a switch 24, an amplifier 17 connected to the coil 14 to amplify a voltage developed across the coil 14, a diode 18 and a capacitor 20 connected to the amplifier 17 to rectify the amplified voltage from the amplifier 17 to convert it to a D.C. voltage, and a comparator 21 to which a D.C. voltage developed at a cathode of the diode 18 is supplied. A reference voltage is supplied from a terminal 22 to the comparator 21, which compares the signal supplied from the diode 18 with the reference voltage. For example, the comparator 21 produces an output voltage at a terminal 23 when the output voltage of the diode 18 is lower than the reference voltage. The oscillator 16 may generate a sine wave or a pulse wave. It preferably generates a signal having a frequency of 100 kHz–500 kHz. In the operation of the frost detector shown in FIG. 7, when the switch 24 is closed, the A.C. current flows from the oscillator 16 to the coil 13 of the frost sensor 30 so that an acoustic wave (LAMB wave) is generated in the magnetostrictive ribbon 12. The acoustic wave propagates through the magnetostrictive ribbon 12 and reaches the coil 14 to produce the A.C. electrical signal in the coil 14. The electrical signal generated in the coil 14 is amplified by the amplifier 17 and the resulting signal is rectified by the diode 18. If frost is not deposited on the magnetostrictive ribbon 12, the acoustic wave generated by the coil 13 reaches the coil 14. As a result, the A.C. signal generated in the coil 14 has a large amplitude and hence the D.C. voltage generated by the diode 18 has a large magnitude. If frost is deposited on the magnetostrictive ribbon 12, little acoustic wave reaches the coil 14 so that the A.C. signal generated in the coil 14 has a small amplitude. Accordingly, the D.C. voltage generated by the diode 18 has a small magnitude. The reference voltage $E_R$ is selected such that $$E_1 > E_R > E_2$$

where $E_1$ is the D.C. voltage developed by the diode 18 when the frost is not deposited on the magnetostrictive ribbon 12 and $E_2$ is the D.C. voltage developed by the diode 18 when the frost is deposited on the magnetostrictive ribbon 12. Accordingly, the output voltage of the comparator 21 changes between when the voltage $E_1$ is supplied to the comparator 21 and when the voltage $E_2$ is supplied thereto. For example, when the voltage $E_2$ is supplied the comparator 21 produces an H-level output signal and when the voltage $E_1$ is supplied, it produces an L-level output signal. Accordingly, by monitoring the output signal of the comparator 21 the presence of the frost deposited on the magnetostrictive ribbon 12 is determined.

Figure 8:
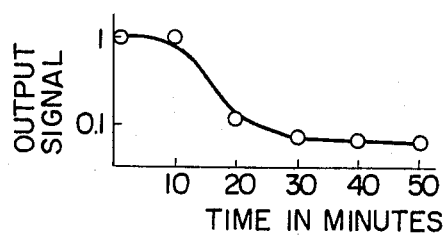
FIG. 8 shows a characteristic curve illustrating a change in an output voltage of the frost sensor of the present invention.

FIG. 8 shows a change in the A.C. voltage generated in the coil 14 when the frost sensor of the present invention is installed in a refrigerator of a freezer. In FIG. 8, an abscissa represents an erapsed time after the frost sensor 30 has been fixed to the refrigerator and an ordinate represents an amplitude of the output voltage generated in the coil 14 with the amplitude of the output voltage developed in the coil 14 when no frost is deposited on the magnetostrictive ribbon 12 being assumed as unity. In measuring the data shown in FIG. 8, water vapor was intentionally introduced into the refrigerator by a humidifier so that frost was readily deposited on the magnetostrictive ribbon 12. While it was attempted to measure a relation between the thickness of the frost deposited on the magnetostrictive ribbon 12 and the output voltage, it was difficult to measure the thickness of the frost. Accordingly, the relationship between the elapsed time and the output voltage as shown in FIG. 8 was measured. After ten minutes of time has elapsed, the output signal of the frost sensor does not substantially change. After twenty minutes, it decreased to approximately one tenth of the initial output voltage. At this time point, a thin frost was observed on the magnetostrictive ribbon 12. The output signal decreases little by little until forty minutes of time has elapsed and no substantial decrease is observed thereafter. At the forty minutes time point, a frost of approximately 1 mm thickness was observed. In the measurement process, the oscillation frequency of the oscillator 16 was 280 kHz and the temperature of the refrigerator of the freezer was approximately −18° C. Since the support member 10 is made of brass having a high thermal conductivity, the frost sensor should have reached the temperature of the refrigerator in a relatively short time period. In the present experiment, since the water vapor was intentionally supplied to the freezer by the humidifier, the frost was deposited on the magnetostrictive ribbon 12 in approximately twenty minutes. In a normal use of the freezer, it will take several hours.

As described above, the present frost sensor is very sensitive because the output voltage developed in the coil 14 decreases by the deposition of the frost of only no more than 1 mm thickness on the magnetostrictive ribbon 12 of the frost sensor 30. When the present frost detector is actually mounted in the refrigerator or the like, if the sensitivity is two high, the frost sensor 30 may be disposed at a position at which the frost is hardly deposited.

An affect of water droplet deposited on the magnetostrictive ribbn 12 of the present frost detector 30 was also measured. Water droplets having a diameter of approximately 2 mm were dropped one at a time on the magnetostrictive ribbon 12 and the amplitude of the output voltage was measured for every other water droplet. The amplitude of the output signal showed substantially no change even after the water droplets were deposited on the entire upper surface of the magnetostrictive ribbon 12.

Figure 9:
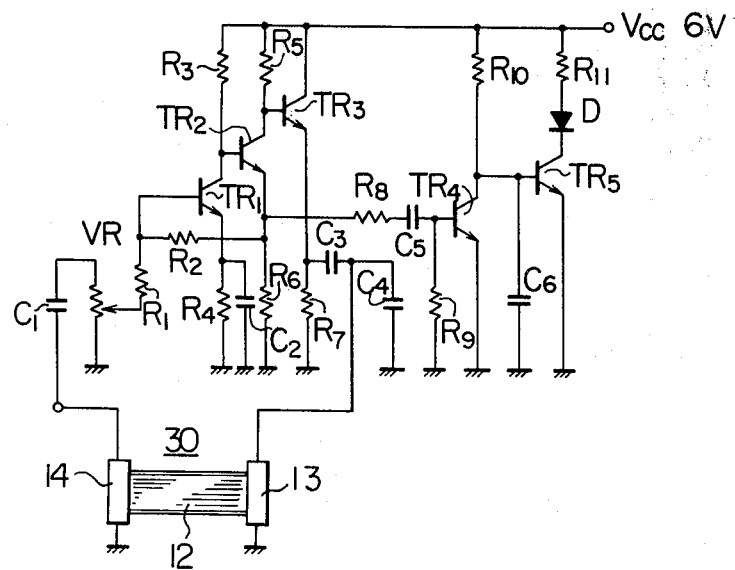
FIG. 9 shows a circuit diagram of a modification of the frost detector.

FIG. 9 shows a modification of the frost detector. In the illustrated frost detector, the frost sensor 30 is used as an oscillating element and is arranged in a positive feedback loop of an amplifier comprising transistors $TR_1$, $TR_2$ and $TR_3$. In FIG. 9, $R_1$-$R_{11}$ denote resistors, $C_1$-$C_6$ denote capacitors, VR denotes a potentiometer, $TR_4$ and $TR_5$ denote transistors and D denotes a light emitting diode. A circuit comprising the frost sensor 30, the transistors $TR_1$-$TR_3$, the resistors $R_1$-$R_7$, the potentiometer VR and the capacitors $C_1$-$C_4$ constitutes an oscillator which oscillates at a frequency of approximately 280 kHz. Since an insertion loss of the frost sensor 30 is approximately 25 dB when no frost is deposited on the magnetostrictive ribbon 12, the oscillation circuit oscillates if the amplifier circuit comprising the transistors $TR_1$-$TR_3$ has a gain of 50 dB. The output signal of the oscillator is supplied from the emitter of the transistor $TR_2$ to the transistor $TR_4$ through the resistor $R_8$ and the capacitor $C_5$. The transistor $TR_4$ is turned on in a positive half cycle of the signal supplied thereto as that the collector voltage of the transistor $TR_4$ drops. If a time constant $T=RC$ of the resistor $R_{10}$ and the capacitor $C_6$ is sufficiently larger than the period of the output signal of the oscillator, the collector voltage of the transistor $TR_4$ does not rise when it is turned off in the negative half cycle of the output signal of the oscillator. Accordingly, the transistor $TR_5$ remains non-conductive and no current flows through the light emitting diode D.

When frost is deposited on the magnetostrictive ribbon 12 of the frost sensor 30, the insertion loss of the frost sensor increases to approximately 50 dB so that the signal produced at the emitter of the transistor $TR_3$ is not substantially fed back to the base of the transistor $TR_1$ and the oscillator stops to oscillate. As a result, the output signal of the oscillator is not supplied to the transistor $TR_4$ and the transistor $TR_4$ is turned on. Consequently, the base voltage of the transistor $TR_5$ rises to turn on the transistor $TR_5$ so that a current flows through the light emitting diode D, which in turn emits light. Since the light emitting diode D emits light only when the frost is deposited on the magnetostrictive ribbon 12 of the frost sensor 30, the presence of the frost can be determined.

As described above, the frost sensor of the present invention detects the presence of the frost directly and with a high sensitivity, is simple in structure, does not need troublesome adjustment and can electrically detect the presence of the frost. In the present frost sensor, the acoustic wave is not deflected by the frozen water droplet deposited on the transducer. The present frost sensor is easy to manufacture because the coils are mounted on the support member after the magnetostrictive ribbon has been fixed to the support member and hence it is not necessary to insert the magnetostrictive ribbon through the coils. The present frost sensor generates only weak biasing magnetic field at the opposite ends of the magnetrostrictive ribbon even when a strong biasing magnetic field is applied to the magnetostrictive ribbon and hence the magnetic fluxes generated by the current flowing through the coil can readily pass through the magnetostrictive ribbon so that the magnetostriction is readily generated. Since a strong biasing magnetic field is applied to the area B of the magnetostrictive ribbon, the magnetic fluxes generated by the acoustic wave exciting coil do not pass through the area B of the magnetrostrictive ribbon resulting in the reduction of the noise.

I claim:

1. A frost sensor for detecting the presence of frost comprising;
   (a) an acoustic transmitting medium for detecting the frost made of a magnetic metal material having a magnetostrictive property and having a ribbon shape, said acoustic transmitting medium being adapted to be disposed in an environment which allows the frost to be detected to be deposited thereon,
   (b) a support member made of a non-magnetic material, the opposite ends of said acoustic transmitting medium being fixedly mounted on said support member with a center portion between said opposite ends of said acoustic transmitting medium extending on said support member, said support member having a permanent magnet arranged in parallel to said center portion and in spaced relation thereto by a predetermined distance,
   (c) a first transducer having a coil wound and mounted on one of said opposite ends of said acoustic wave transmitting medium fixedly mounted on said support member, said first transducer generating an acoustic wave in said acoustic transmitting medium in response to the application of a current to said coil,
   (d) a second transducer having a coil wound and mounted on the other end of said acoustic transmitting medium fixedly mounted on said support member, said second transducer transducing said acoustic wave to an electrical signal, and
   (e) said permanent magnet being fixedly mounted to extend in parallel to said center portion of said acoustic transmitting medium and in spaced relation thereto by the predetermined distance, said permanent magnet applying a biasing magnetic field to said acoustic transmitting medium.

2. A frost sensor according to claim 1, wherein said support member includes supports for fixedly supporting said opposite ends of said acoustic transmitting medium and a base extending between said supports, said center portion of said acoustic transmitting medium spanning over said base, said base supporting said permanent magnet in parallel to said center portion and in spaced relation thereto by the predetermined distance.

3. A frost sensor according to claim 1 or 2, wherein said permanent magnet is a bar magnet having a length not exceeding the length of said center portion of said acoustic transmitting medium spanning over said support member.

4. A frost sensor according to claim 1 or 2, wherein said support member supports said permanent magnet at positions spaced from said center portion of said acoustic transmitting medium in the direction of the thickness of said acoustic transmitting medium.

5. A frost sensor according to claim 1 or 2, wherein said support member supports said permanent magnet at positions spaced from said center portion of said acoustic transmitting medium in the direction of the width of said acoustic transmitting medium.

6. A frost sensor according to claim 1 or 2, wherein said acoustic transmitting medium is made of an amorphous metal alloy.

7. A frost sensor according to claim 6, wherein said amorphous metal alloy consists of iron, nickel, silicon and boron.

8. A frost sensor according to claim 7, wherein said amorphous metal alloy consists of iron, nickel, silicon, boron, chromium and phosphorous.

9. A frost sensor according to claim 2, wherein said support member has a flat base and legs provided at opposite ends of said base, said acoustic transmitting medium being disposed on said legs, a surface of said base being in parallel to said center portion of said acoustic transmitting medium such that the surface of said base faces said center portion, and surfaces of said legs having said acoustic transmitting medium disposed thereon being in parallel to the surface of said base.

10. A frost sensor according to claim 1, wherein said first transducer generates a LAMB acoustic wave in said acoustic transmitting medium.

11. A frost sensor according to claim 1, further comprising means for determining the magnitude of the output signal of said second transducer.

* * * * *